United States Patent
Lefebvre

(10) Patent No.: US 11,439,596 B2
(45) Date of Patent: Sep. 13, 2022

(54) CO-GRANULES OF XANTHAN GUM AND ACACIA GUM

(71) Applicant: Societe d'Exploitation de Produits Pour les Industries Chimiques Seppic, Paris (FR)

(72) Inventor: Sandra Lefebvre, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 15/308,697

(22) PCT Filed: Apr. 28, 2015

(86) PCT No.: PCT/FR2015/051149
§ 371 (c)(1),
(2) Date: Nov. 3, 2016

(87) PCT Pub. No.: WO2015/170038
PCT Pub. Date: Nov. 12, 2015

(65) Prior Publication Data
US 2017/0189336 A1    Jul. 6, 2017

(30) Foreign Application Priority Data

May 5, 2014   (FR) ..................... 1454061

(51) Int. Cl.
*A61K 9/20*   (2006.01)
*A61K 9/16*   (2006.01)
*A61K 47/36*  (2006.01)

(52) U.S. Cl.
CPC ............ *A61K 9/205* (2013.01); *A61K 9/1652* (2013.01); *A61K 47/36* (2013.01)

(58) Field of Classification Search
CPC ....... A61K 47/36; A61K 9/1652; A61K 9/205
See application file for complete search history.

(56) References Cited

U.S. PATENT DOCUMENTS

| 6,221,393 B1 | 4/2001 | Collaueri et al. |
| 2009/0175941 A1 | 7/2009 | Francas |
| 2014/0322321 A1 | 10/2014 | Herry et al. |

FOREIGN PATENT DOCUMENTS

| EP | 0 206 368 A2 | 12/1986 |
| EP | 0 360 562 A2 | 3/1990 |
| EP | 0 805 676 B1 | 11/1997 |
| FR | 2 983 409 A1 | 7/2013 |
| GB | 2 086 204 A | 5/1982 |

OTHER PUBLICATIONS

Desplanques et al., Food Hydrocolloids, vol. 27, pp. 401-410 (Year: 2012).*
Rowe, R.C. et al., editors, "Xantham Gum," Handbook of Pharmaceutical Excipients, Seventh Edition, 2012, p. 897.
Wen, H. et al., editors, "Oral Controlled Release Formulation Design and Drug Delivery: Theory to Practice," Sep. 2010.
Talukdar, M.M. and Kinget, R., "Swelling and drug behaviour of xantham gum matrix tablets," International Journal of Pharmaceuticals 120 (1995) 63-72.
Mikac, U. et al., "A new approach combining different MRI methods to provide detailed view on swelling dynamics of xanthan tablets influencing drug release at different pH and ionic strength,"Journal of Controlled Release 145 (2010) 247-256.

* cited by examiner

*Primary Examiner* — Kara R McMillian
(74) *Attorney, Agent, or Firm* — Nixon & Vanderhye

(57) ABSTRACT

The invention relates to a co-granule of xanthan gum and acacia gum having an average diameter of between 50 μm and 1000 μm.

10 Claims, 1 Drawing Sheet

CO-GRANULES OF XANTHAN GUM AND ACACIA GUM

BACKGROUND OF THE INVENTION

A subject of the invention is co-granules of xanthan gum and acacia gum, used to prepare pharmaceutical compositions, food supplement compositions or dietary compositions in the form of prolonged-release (also referred to as delayed-effect) tablets and the method for preparing same.

Said pharmaceutical, food supplement or dietary compositions contain a pharmacologically active ingredient and/or a nutritional agent and are for example used when it is desired to administer a medication to a patient over a prolonged period without requiring the patent to take repeated doses with short intervals.

The "Handbook of pharmaceutical excipients 7th Edition, 2012" describes the different possible applications for xanthan gum. The latter is widely used as a thickening agent. Synergistic combinations have been highlighted between xanthan gum and galactomannans (guar gum, locust bean gum, cassia gum, etc.), making it possible to obtain very high viscosity gels.

Xanthan gum is an excipient known in the fields of pharmaceuticals and nutrition for its use in formulating prolonged-release tablets (also referred to as hydrophilic matrices). In the book "Oral Controlled Release Formulation Design and Drug Delivery: Theory to Practice. Edited by Hong Wen—Kinam Park. September 2010", a definition of a prolonged-release tablet is given.

This is a tablet formulated such that the active ingredient is released over a defined period of time after exposure to an aqueous medium or after oral administration. Such a tablet conventionally consists of an active ingredient or a mixture of active ingredients and/or a nutritional agent or a mixture of nutritional agents, at least one thickening polymer, technological additives, such as, for example, a diluent, a lubricant and a flow agent, and is manufactured by direct compression of the mixture of all of its constituents.

Direct compression is a particularly advantageous method for galenical forming since it involves a limited number of operations and constituents and, consequently, carrying it out requires less expensive facilities than a method for preparing tablets by wet granulation.

Through the publications: "Comparative study on xanthan gum and hydroxypropylmethylcellulose as matrices for controlled-release drug delivery I, Compaction and in vitro drug release behavior", *International Journal of Pharmaceutics* 129 (1996) 233-241; and "Swelling and drug release behaviour of xanthan gum matrix tablets", *International Journal of Pharmaceutics* 120 (1995) 63-72, Mohammad Mahiuddin Takudar of the University of Louvain has widely studied the formulation of prolonged-release tablets using xanthan gum as thickening polymer. Combinations of xanthan gum/galactomannans have also been tested by different scientists.

Natural or synthetic hydrophilic gums which are high molecular weight polysaccharides are known as pharmaceutical excipients, but not all gums can be used in prolonged-effect compositions in dry compression methods for preparing the tablets.

These polysaccharides are either of microbial origin, and in this case are obtained by fermentation of a carbohydrate which can be assimilated by a suitable microorganism (for example: xanthan gum obtained from *Xanthomonas campesiris*), or of natural origin such as, for example, guar gum and locust bean gum.

Xanthan gums are also excipients known for their possible use in the pharmaceutical field, especially to constitute matrices intended for the preparation of controlled-release forms. However, hydrophilic gums in general and xanthan gum in particular are not generally used in the pre-granulate state.

EP0805676 describes the use of xanthan gum, especially at a high content (generally at a content of approximately 30 weight % per 100% of the total weight of the tablet), leading to a hydrophilic matrix, which nonetheless has numerous defects such as poor mechanical properties, etc.

BRIEF SUMMARY OF THE INVENTION

One aim of the present invention is to prepare a prolonged-effect tablet which may be manufactured easily by direct compression and which has good properties of release of the active ingredient and better mechanical properties than those described in the prior art, for example in patent EP0805676.

It is for this reason that a subject of the present invention is a co-granule of xanthan gum and acacia gum, having a mean diameter of between 50 µm and 1000 µm.

DETAILED DESCRIPTION OF THE INVENTION

Figure 1:
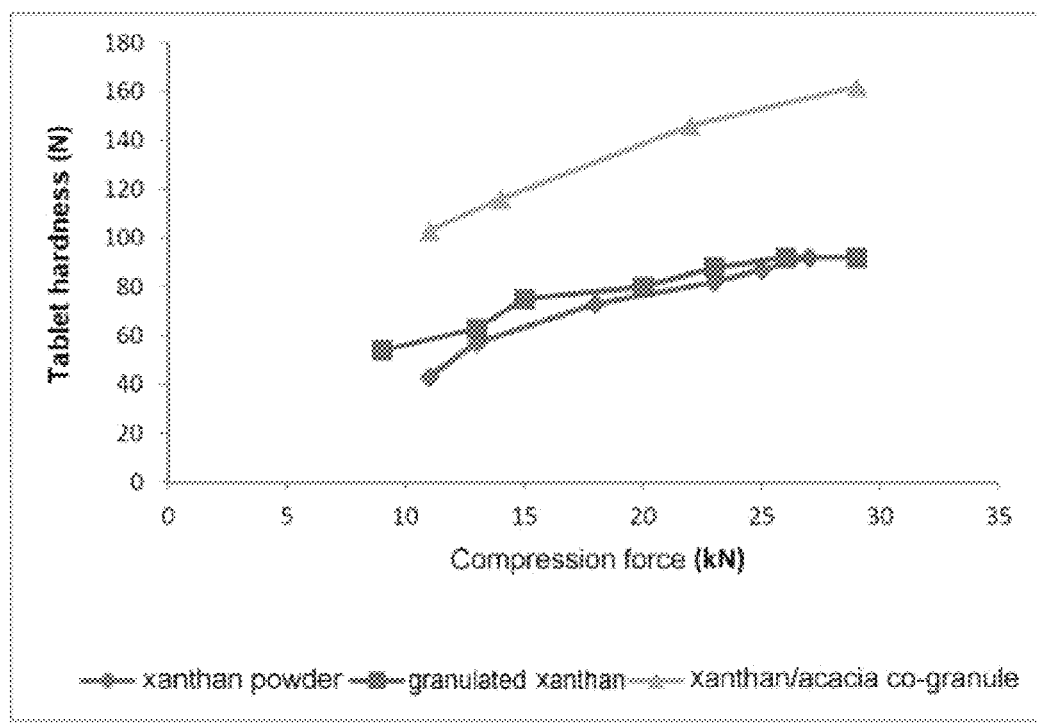
FIG. 1 shows hardness of tablets as a function of compression force.
Figure 2:
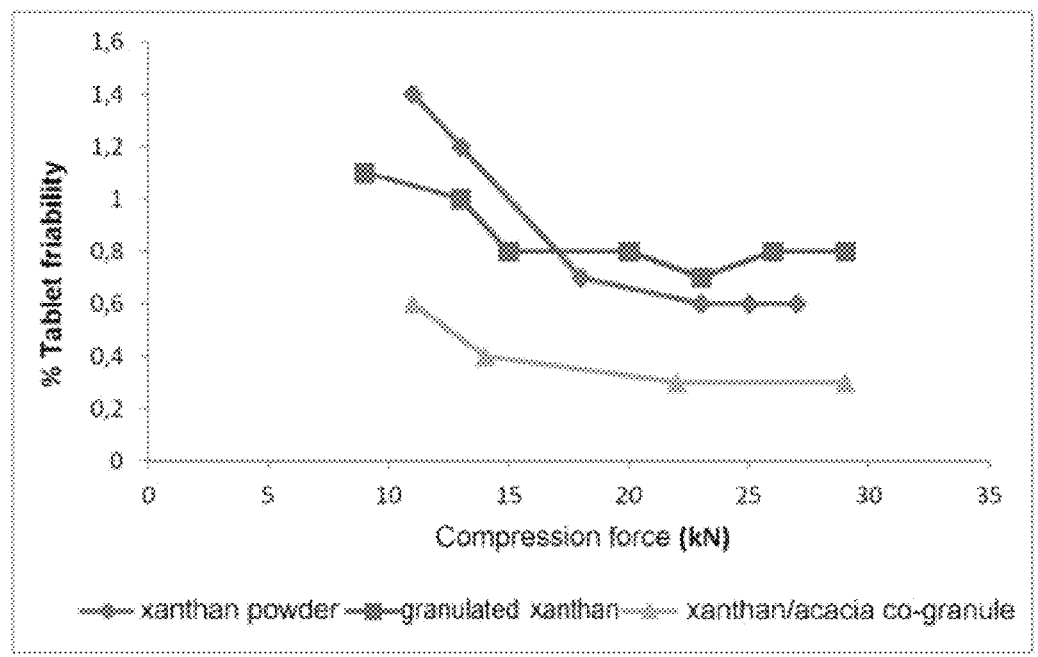
FIG. 2 show friability of tablets as a function of compression force.

In the products which are subjects of the present invention, xanthan gum is used to denote a heteropolymer of monosaccharides and uronic acids, obtained by aerobic fermentation by bacteria of the genus *Xanthomonas campestris*. Its structure consists of a main chain of β-D-glucose units connected to one another by the 1 and 4 carbons.

There is one branched triholoside every two glucose units in the main chain, in a regular alternating manner; each branch consists of a triholoside composed of two mannoses and a glucuronic acid, of the type: β-d-Manp-(1→4)-β-d-GlcAp-(1→2)-α-d-Manp-(1→3).

Xanthan gums are available in the form of a salt of sodium, potassium or calcium, and are characterized by a molecular weight between 1 000 000 and 50 000 000.

Xanthan gums are represented for example by the products sold under the trade name Rhodicare™ by Rhodia Chimie and under the brand name Keltrol™ CG-T by CP-KELCO.

In the products which are subjects of the present invention, acacia gum is used to denote a complex, branched heteropolymer of monosaccharides and uronic acids, the main chain of which consists of β-D-galactose units connected to one another by the 1 and 3 carbons.

The chains branched to the main chain consist of β-D-galactose units connected to one another by the 1 and 6 carbons, also bearing α-arabinose units, and to a lesser extent β-glucoronosyl units. Both the main chain and the pendent chains contain α-L-arabinosyl, α-L-rhamnopyranosyl, β-D-glucuronopyranosyl and 4-O-methyl-β-D-glucuronopyranosyl units.

Acacia gum is also denoted by the name "gum arabic" and is a solidified exudate of phloem sap, amalgamated naturally or by incision into the trunk and base of trees of the acacia family.

The acacia gum used in the present invention is represented for example by the product sold under the trade name Efficacia™ M by Colloïdes Naturels International.

According to a particular aspect, a subject of the present invention is:
- a co-granule as defined above, having a mean diameter of between 100 µm and 300 µm, preferably equal to approximately 150 µm.
- a co-granule as defined above, characterized in that at most 4 weight % of the particles of the co-granule have a mean diameter of greater than 500 µm and from 65 to 90 weight % of the particles of the co-granule have a mean diameter of greater than 80 µm (European Pharmacopeia, 8th Edition 2014 (method 2.9.38)).
- a co-granule as defined above, having a density of between 0.3 mg/ml and 0.8 mg/ml and preferably of between 0.35 mg/ml and 0.7 mg/ml (European Pharmacopeia, 8th Edition 2014 (method 2.9.34)).
- a co-granule as defined above, characterized in that the weight ratio between the xanthan gum and the acacia gum varies from 4/1 to 1/1 and is preferably equal to 3/1.

Another subject of the present invention is:
- a composition comprising at least one tablet containing at least one active ingredient and/or at least one nutritional agent, characterized in that said tablet comprises from 15 to 50 weight % of co-granules, and preferably from 20% to 40%, as defined above.
- a composition as defined above, characterized in that the tablet also comprises at least one excipient chosen from at least: a diluent, a lubricant, a cohesion agent.
- a composition as defined above, characterized in that it comprises, per 100% of its weight, from 20 to 35 weight % of co-granules as defined above, from 0.1 to 60 weight % of an active ingredient and/or of a nutritional agent, from 10 to 50 weight % of diluent or cohesion agent, and from 0.5 to 3 weight % of lubricant.
- a composition as defined above, characterized in that it is a pharmaceutical, food supplement or dietary composition, having a prolonged-release effect.

Another subject of the present invention is:
- a method for preparing a composition as defined above, comprising at least one step of direct compression of a mixture comprising from 15% to 50% by weight of co-granules as defined above, preferably from 20% to 40%, and at least one active ingredient and/or at least one nutritional agent.
- a method as defined above, wherein said composition also comprises at least one excipient chosen from at least: a diluent, a lubricant, a cohesion agent.

Another subject of the present invention is:
The use of at least one co-granule as defined above, for the manufacture of a pharmaceutical composition or a food supplement or dietary composition as defined above.

The tablets of the composition which is a subject of the present invention are characterized by:
- as high a breaking strength as possible (ideally>90 N);
- as low a friability as possible (ideally<0.5%);
- a gradual release of the active ingredient after exposure to an aqueous medium (disaggregation time of the tablet>1 h).

The prolonged-release tablets produced with the co-granules comprising xanthan gum and acacia gum have markedly better mechanical properties than the prolonged-release tablets manufactured with only xanthan gum in powder form or only granulated xanthan gum (cf example 2).

The co-granule of the present invention will contain, per 100% of its weight, at least 20 weight % of acacia gum and therefore at most 80 weight % of xanthan gum.

This minimum content of 20 weight % of acacia gum makes it possible to guarantee that the prolonged-release tablets manufactured have a high breaking strength (cf example 1).

The co-granule of the present invention will contain, per 100% of its weight, at least 50 weight % of xanthan gum. This minimum content of 50 weight % of xanthan gum makes it possible to guarantee a gradual release of the active ingredient after exposure to an aqueous medium (cf example 3).

Within the context of the present invention, the term "co-granule" does not mean a simple mixture of at least two compounds, but a combination in which the compounds are intimately connected. In other words, the essential constituents of the co-granules are at least physically connected to one another.

The co-granules of the present invention may be prepared by any of the means available for bringing an acacia gum solution and solid particles of xanthan gum into contact (granulator, fluidized air bed, atomizer, rotary drum, spray-drying towers, etc.).

There are numerous methods described in the literature for preparing co-granules.

Among these known methods, mention may be made of U.S. Pat. No. 3,551,133 describing a method for preparing co-granules of xanthan gum and locust bean gum by spraying an aqueous solution of a mixture of powder of the two gums onto inclined-plate or disk granulators.

GB-2086204 describes a method of the same type.

According to EP-206 368, a solution of gums is sprayed onto a fluidized bed of gums.

The preferred granulation method is, according to the invention, the method according to which a solution of acacia gum is sprayed onto the xanthan gum, in a fluidized bed by means of a gas stream, and the granules are obtained by drying.

However, the prolonged-release tablet may also comprise one or more pharmaceutically and/or nutritionally acceptable excipients, more particularly diluents, cohesion agents, lubricants.

Among the diluents which may be combined in the prolonged-release tablet, mention may be made of lactose, sucrose, mannitol, xylitol, isomalt, calcium hydrogen phosphate, microcrystalline cellulose, starches, and more particularly pregelatinized starches, calcium and magnesium carbonates, etc.

Among the lubricants which may be combined in the prolonged-release tablet, mention may be made of magnesium stearate, talc, sodium stearyl fumarate, hydrogenated vegetable oils, stearic acid, etc.

The present invention may be used for the direct compression of nutritional agents and active ingredients belonging to all classes of medications intended for oral administration.

Among the active ingredients used in compositions according to the present invention, mention may be made of nonsteroidal anti-inflammatories and antirheumatics (ketoprofen, ibuprofen, flurbiprofen, indomethacin, phenylbutazone, allopurinol, etc.), analgesics (paracetamol, phenacetin, aspirin, etc.), antitussives (codeine, codethyline, alimemazine, etc.), sterols (hydrocortisone, cortisone, progesterone, testosterone, triamcinolone, dexamethazone, betamethazone, paramethazone, fluocinolone, beclomethazone, etc.), barbiturates (barbital, allobarbital, phenobarbital, pentobarbital, amobarbital, etc.), antimicrobials (pefloxacin, sparfloxacin, and derivatives of the class of quinolones, tetracyclines, synergistins, metronidazole, etc.), medications intended for treating allergies, antiasthmatics, vitamins (vitamin A, vitamin E, vitamins of the D group, vitamin K), antispasmodics and antisecretory agents (omeprazole), cardiovascular agents and cerebral vasodilators (quinacainol, oxprenolol, propanolol, nicergotine, etc.), cerebroprotective agents, hepatic protective agents, therapeutic agents for the gastrointestinal tract, vaccines, antihypertensives and cardioprotective agents, such as beta blockers and nitro derivatives. Among the nutritional agents used in compositions according to the present invention, mention may be made of mineral salts (calcium, magnesium, iron, zinc, sodium, potassium, copper, manganese, etc.), plant extracts (burdock, borage, lemon balm, hops, lavender, white deadnettle, cherry stalk, meadowsweet, ginseng, guarana, ginger, passion flower, valerian, hawthorn, lime, verbena, etc.) and fatty acids (omega 3, omega 6).

According to the invention, the compression operation following mixing of the excipients and the active ingredient or nutritional agent is generally carried out under a force which may range from 6 to 20 kN (measured at the compression roller) and preferably of the order of 8 to 12 kN.

This compression operation is preferably preceded by a pre-compression under a force which may range from 0.5 to 2.5 kN.

High compression rates may be achieved by virtue of the method according to the invention, without however adversely affecting the quality of the tablets. It is especially possible to achieve rates of greater than 150 000 tablets per hour, without causing any splitting.

It is understood that the tablets obtained according to the invention may optionally be film-coated according to customary methods. The film-coating operation is facilitated by the fact that no splitting occurs during the operation.

In the following text or the above text, unless indicated otherwise, the percentages and parts are by weight.

The following examples illustrate the present invention without, however, limiting it.

PROCEDURE FOR PREPARING TABLETS 700 g of the powder mixture consisting of an active ingredient, in this case synthetic caffeine, and the various matrix constituents, namely the xanthan gum-acacia gum co-granule, and optionally the other excipients, such as for example dicalcium phosphate, are mixed beforehand in a Turbula T2c type mixer. The powder mixture also contains the lubricant, name magnesium stearate metered in at 1% by weight to said mixture.

The compression is carried out under a force of 8.5 kN (measured at the compression roller) using a rotary machine of Picola Nova type, which makes it possible to produce, from the powder mixture, 1000 tablets, each of 500 mg.

EXAMPLES

Example 1

Co-granules containing different proportions by weight of xanthan gum and acacia gum were manufactured.

Prolonged-release tablets were prepared with these co-granules according to the following composition:

| Mixture composition: | Formula (%): |
|---|---|
| Co-granules | 35% |
| Synthetic caffeine | 20% |
| CMC (carboxymethyl cellulose) Vivapur (JRS) | 33% |
| Calcium Hydrogen Phosphate dihydrate Ph Eur Emcompress (JRS) | 11% |
| Mg stearate | 1% |

The breaking strength of the tablets was controlled according to the methods of the European Pharmacopeia, 8th Edition 2014 (method 2.9.8).

| Co-granule composition by weight: | | | | |
|---|---|---|---|---|
| % xanthan | 100% | 90% | 80 | 75 |
| % acacia | 0% | 10% | 20 | 25 |
| Breaking strength of the tablets (N) | 72 | 78 | 91 | 103 |

At least 20% acacia gum in the co-granule makes it possible to obtain tablets with a breaking strength of greater than 90 N.

Example 2

Prolonged-release tablets with 2 types of commercially available gum were formulated:
  Xanthan gum powder (mean particle diameter: 74 μm)
  Granulated xanthan gum (mean particle diameter: 185 μm)

In parallel, prolonged-release tablets were manufactured with the co-granules of xanthan gum and acacia gum (75/25 w/w) of mean diameter: 150 μm.

The same compression formula was used:

| Mixture composition: | Formula (%): |
|---|---|
| Xanthan-acacia co-granules, or xanthan gum powder, or granulated xanthan gum | 35% |
| Synthetic caffeine | 20% |
| CMC (JRS) Vivapur | 33% |
| Calcium Hydrogen Phosphate dihydrate Ph Eur. Emcompress (JRS) | 11% |
| Mg stearate | 1% |

The mixtures were compressed on the Picola Noca rotary press with the following parameters:
  8 punches 11 mm in diameter
  targeted weight: 500 mg/tablet
  Various compression forces were tested.

The breaking strength of the tablets and their friability were controlled according to the methods of the European Pharmacopeia, 8th Edition 2014 (methods 2.9.7 and 2.9.8).

The following results were obtained with the xanthan gum powder:

| Compression force (kN) | Breaking strength of the tablets (N) | % friability of the tablets |
|---|---|---|
| 11 | 43 | 1.4 |
| 13 | 57 | 1.2 |

-continued

| Compression force (kN) | Breaking strength of the tablets (N) | % friability of the tablets |
|---|---|---|
| 18 | 73 | 0.7 |
| 23 | 82 | 0.6 |
| 25 | 87 | 0.6 |
| 27 | 92 | 0.6 |

Results with granulated xanthan gum:

| Compression force (kN) | Breaking strength of the tablets (N) | % friability of the tablets |
|---|---|---|
| 9 | 54 | 1.1 |
| 13 | 63 | 1.0 |
| 15 | 75 | 0.8 |
| 20 | 80 | 0.8 |
| 23 | 88 | 0.7 |
| 26 | 92 | 0.8 |
| 29 | 92 | 0.8 |

Results with xanthan/acacia (75/25) co-granule:

| Compression force (kN) | Breaking strength of the tablets (N) | % friability of the tablets |
|---|---|---|
| 11 | 103 | 0.6 |
| 14 | 116 | 0.4 |
| 22 | 142 | 0.4 |
| 29 | 162 | 0.4 |

FIGS. 1 (hardness of the tablets as a function of the compression force) and 2 (friability of the tablets as a function of the compression force) illustrate that at equal compression force, the tablets manufactured with the xanthan/acacia co-granule have better mechanical properties than the tablets with xanthan gum: a higher breaking strength and a lower friability.

This applies irrespective of the particle size of the control xanthan gum (powder or granulated).

Example 3

Co-granules containing different proportions by weight of xanthan gum and acacia gum were manufactured. Tablets were prepared with these co-granules according to the following composition:

| Mixture composition: | Formula (%): |
|---|---|
| Co-granules | 35% |
| Synthetic caffeine | 20% |
| CMC Vivapur (JRS) | 33% |
| Calcium Hydrogen Phosphate dihydrate Ph Eur. Emcompress (JRS) | 11% |
| Mg stearate | 1% |

The disaggregation time of the tablets was controlled according to the methods of the European Pharmacopeia, 8th Edition 2014 (method 2.9.1).

| Co-granule composition by weight | | | |
|---|---|---|---|
| % xanthan | 100% | 75 | 50 |
| % acacia | 0% | 25 | 50 |
| Disaggregation time of the tablets (N) | >7 hours | 6.5 hours | 90 minutes |

At least 50% xanthan gum in the co-granule makes it possible to obtain prolonged-release tablets.

The invention claimed is:

1. A co-granule consisting of:
xanthan gum and acacia gum,
wherein the co-granule has a mean diameter of between 100 μm and 300 μm, and
a density of between 0.35 mg/ml and 0.7 mg/ml,
wherein at most 4 weight % of the particles of the co-granule have a mean diameter of greater than 500 μm and from 65 to 90 weight % of the particles of the co-granule have a mean diameter of greater than 80 μm,
wherein the weight ratio between the xanthan gum and the acacia gum varies from 4/1 to 3/1, and
wherein said co-granule is prepared by spraying a solution of acacia gum onto solid particles of xanthum gum in a fluidized bed by means of a gas stream, and the co-granules are obtained by drying.

2. The co-granule as claimed in claim 1, wherein the weight ratio between the xanthan gum and the acacia gum is equal to 3/1.

3. A composition comprising at least one tablet wherein said at least one tablet comprise at least one active ingredient and/or at least one nutritional agent, and from 15 to 50 weight % of the co-granules as defined in claim 1.

4. The composition as claimed in claim 3, wherein the at least one tablet further comprises at least one excipient the group consisting of: a diluent, a lubricant, and a cohesion agent.

5. The composition as claimed in claim 4, the at least one tablet comprises, per 100% of its weight, from 20 to 35 weight % of the co-granules, from 0.1 to 60 weight % of an active ingredient and/or of a nutritional agent, from 10 to 50 weight % of the diluent or the cohesion agent, and from 0.5 to 3 weight % of the lubricant.

6. The composition as claimed in claim 3, wherein the composition is a pharmaceutical, food supplement or dietary composition, having a prolonged-release effect.

7. A method for preparing a composition as defined in claim 3, comprising at least one step of forming the at least one tablet by direct compression of a mixture comprising from 15% to 50% by weight of the co-granules and the at least one active ingredient and/or the at least one nutritional agent.

8. The method as claimed in claim 7, wherein the mixture from which the at least one tablet is formed further comprises at least one excipient selected from the group consisting of: a diluent, a lubricant, and a cohesion agent.

9. The method as claimed in claim 7, wherein the composition is a pharmaceutical composition or a food supplement or dietary composition.

10. The co-granule of claim 1, wherein the mean diameter is approximately 150 μm.

* * * * *